(12) United States Patent
Kuhn et al.

(10) Patent No.: US 7,914,315 B2
(45) Date of Patent: Mar. 29, 2011

(54) COUPLING BETWEEN A MEDICAL HANDPIECE PART AND A SUPPLY HOSE

(75) Inventors: Bernhard Kuhn, Biberach (DE);
Thomas Classen, Herbertingen (DE);
Alexander Klee, Biberach (DE)

(73) Assignee: Kultenbach & Voigt GmbH, Biberach (DE)

( * ) Notice: Subject to any disclaimer, the term of this patent is extended or adjusted under 35 U.S.C. 154(b) by 0 days.

(21) Appl. No.: 12/160,244

(22) PCT Filed: Oct. 31, 2007

(86) PCT No.: PCT/EP2007/009462
§ 371 (c)(1),
(2), (4) Date: Aug. 26, 2008

(87) PCT Pub. No.: WO2008/052768
PCT Pub. Date: May 8, 2008

(65) Prior Publication Data
US 2010/0221676 A1    Sep. 2, 2010

(30) Foreign Application Priority Data

Oct. 31, 2006 (DE) .......................... 10 2006 051 511

(51) Int. Cl.
*H01R 13/625* (2006.01)
*H01R 4/50* (2006.01)
(52) U.S. Cl. ........................................ 439/345; 439/192
(58) Field of Classification Search .................. 439/660, 439/680, 192, 489, 345, 490, 271; 433/29, 433/126, 80
See application file for complete search history.

(56) References Cited

U.S. PATENT DOCUMENTS

| 4,515,564 A | 5/1985 | Lohn |
| 4,669,982 A | 6/1987 | Fleer et al. |

(Continued)

FOREIGN PATENT DOCUMENTS

AT           389633           1/1990

(Continued)

OTHER PUBLICATIONS

International Search Report for PCT/EP2007/009462 dated Feb. 26, 2008.

*Primary Examiner* — Javaid Nasri
(74) *Attorney, Agent, or Firm* — Marshall, Gerstein & Borun LLP

(57) ABSTRACT

A coupling for the production of a releasable connection between a medical, in particular a dental, handpiece part and a supply hose and for the transmission of current and if applicable further supply media from the supply hose to the handpiece part. The coupling includes two coupling elements wherein one of the two coupling elements may be arranged on the supply hose and the other on the handpiece part. A guide element is arranged on one of the two coupling elements, which guide element can be inserted into an insertion opening formed on the other coupling element. In a certain relative rotational position of the two coupling elements a pushing element having current contacts engages into a corresponding recess of the second coupling element, wherein with inserted or at least partly inserted guide element the two coupling elements can be rotated relative to one another around an axis of rotation before attainment of the predetermined coupling position. Thereby there is formed a reliable bayonet coupling which makes possible a particularly easy handling.

18 Claims, 9 Drawing Sheets

U.S. PATENT DOCUMENTS

| | | | | |
|---|---|---|---|---|
| 4,680,011 | A | * | 7/1987 | Boinot .......................... 433/29 |
| 4,720,266 | A | * | 1/1988 | Leonard et al. ............... 433/126 |
| 4,725,231 | A | * | 2/1988 | Boinot et al. .................. 433/29 |
| 4,900,252 | A | | 2/1990 | Liefke et al. |
| 5,501,596 | A | | 3/1996 | Bailey |
| 6,159,004 | A | | 12/2000 | Rosenstatter |
| 6,319,003 | B2 | * | 11/2001 | Mosimann ................... 433/126 |
| 2001/0031442 | A1 | | 10/2001 | Mosimann |
| 2004/0166464 | A1 | | 8/2004 | Schneider |

FOREIGN PATENT DOCUMENTS

| | | |
|---|---|---|
| DE | 3215207 | 11/1983 |
| EP | 0185290 | 6/1986 |
| EP | 1145688 | 10/2001 |
| FR | 2584918 | 1/1987 |
| FR | 2592299 | 7/1987 |

* cited by examiner

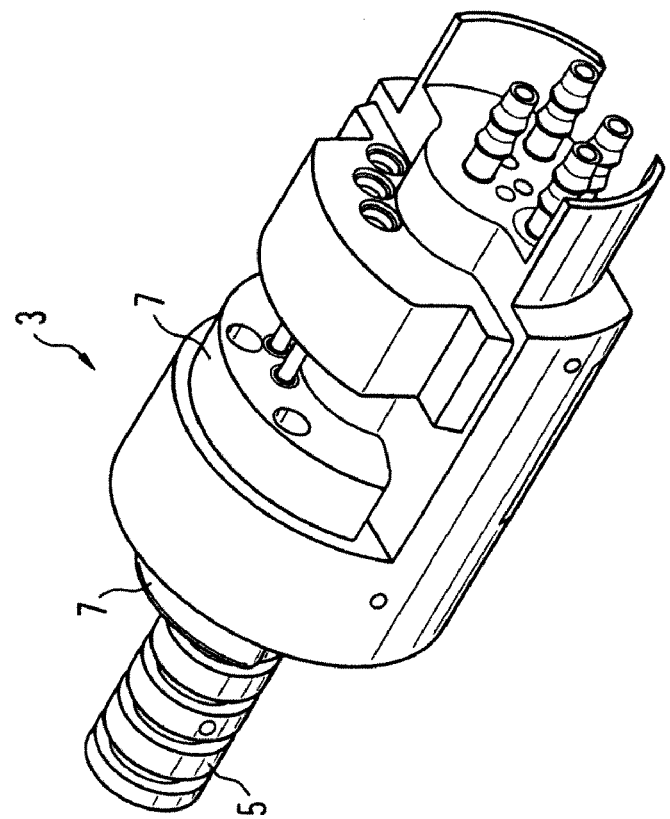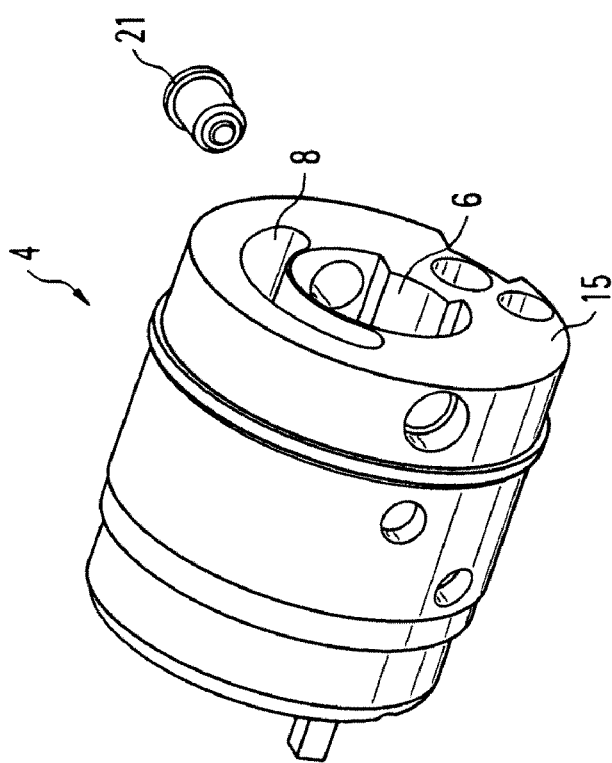
Fig. 1

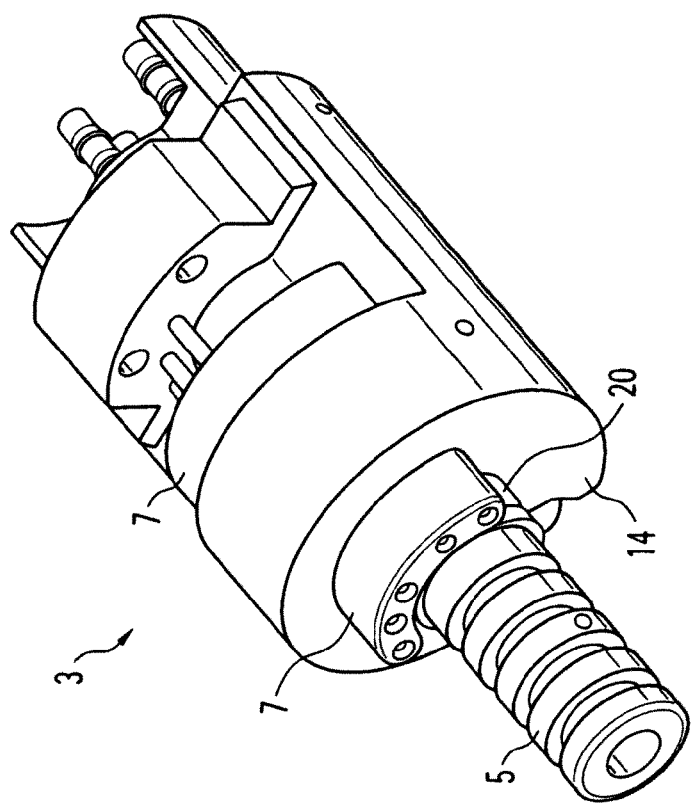
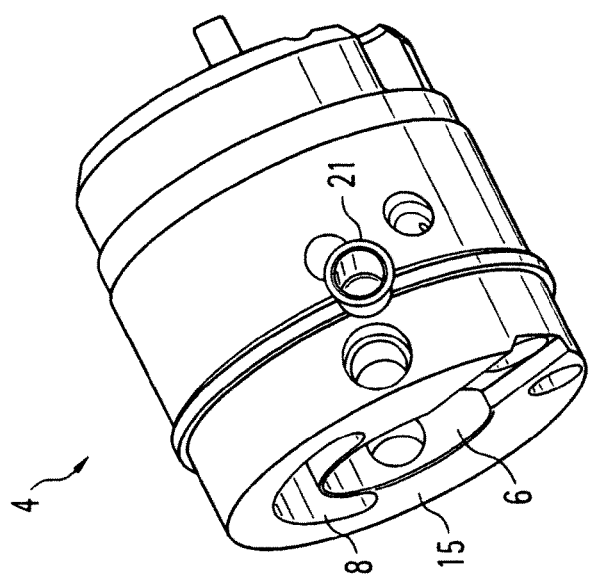
Fig. 3
Fig. 2

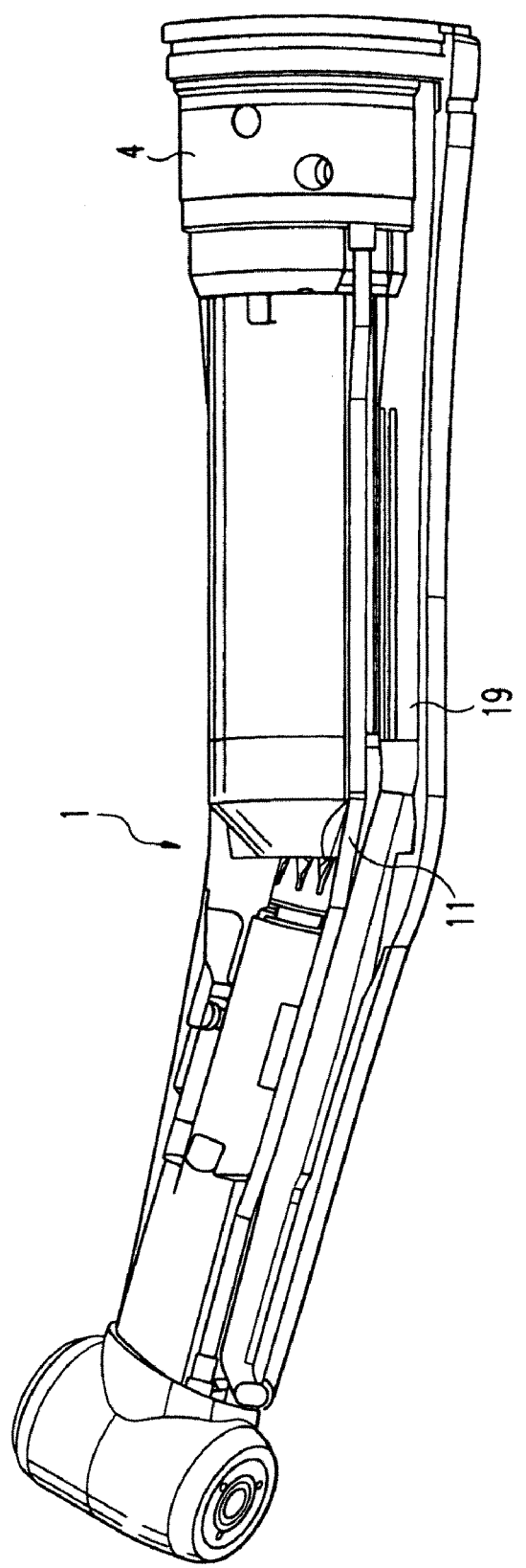

COUPLING BETWEEN A MEDICAL HANDPIECE PART AND A SUPPLY HOSE

BACKGROUND OF THE INVENTION

1. Field of the Invention

The present invention relates to a coupling for the production of a releasable connection between a medical, in particular a dental, handpiece part and a supply hose, and for the transmission of current and if applicable further supply media from the supply hose to the handpiece part.

2. Related Technology

For connection between a dental handpiece part, which may be an angled piece for example, and a supply hose, which serves for the supply of the handpiece part with supply media, such as for example air, water, current or light, it is known to provide a coupling which consists of two coupling elements, wherein one of the two coupling elements is arranged on the handpiece part and the other on the supply hose. For connection, these two coupling elements must be inserted into one another in a certain relative position, in order to connect the media lines for air, water etc. Then, to secure the connection, a lock nut arranged on the one coupling element must then be screwed onto a thread on the other coupling element.

For the production of this connection it is thus necessary that initially the two coupling elements are brought to a certain relative position. In addition, a separate operating step has to be carried out to secure the connection.

A coupling of the kind described above is known from EP 0 185 290 B1, for example. With this known coupling, ring-like channels are provided for the transmission of air and water, which actually make possible a media transmission in any rotational position, however there are used for current transmission inter alia two end face contact pairs. Through this a corresponding current transmission is possible only in a suitable rotational disposition of the two coupling elements, which—as described above—makes handling more difficult.

Further couplings for dental handpieces are known from EP 1 145 688 A1 and DE 32 15 207 A1, in which current transmission is effected with the aid of ring-like sliding contacts. Although these make possible a current transmission in any disposition of the coupling elements with respect to one another, and thus simplify handling, plug contacts are however to be preferred for a durable and reliable current transmission.

GENERAL DESCRIPTION OF THE INVENTION

The present invention therefore provides a corresponding coupling with which in particular an electrical connection between a handpiece part and a supply hose can be made more easily.

In accordance with the present invention there is provided a coupling for the production of a releasable connection between a medical, in particular a dental, handpiece part and a supply hose and for the transmission of current and if applicable further supply media from the supply hose to the handpiece part. The coupling includes a first and a second coupling element, wherein one of the two coupling elements may be arranged on the supply hose and the other on the handpiece part. Thereby, at least one guide element is arranged on one of the two coupling elements and there is formed on the other coupling element at least one insertion opening into which the guide element can be inserted axially, wherein the two coupling elements, with inserted guide element or at least partly inserted guide element, can be rotated relative to one another around an axis of rotation before reaching a mutual rotational position in which a predetermined coupling position is assumed. Preferably, with completely inserted guide element, the two coupling elements are arrested in axial direction.

The handpiece part may include a medical, in particular dental, treatment instrument; that is, for example, an angled piece or a straight handpiece on which, at a forward end, there is arranged a treatment tool for example in form of a drill or the like. A motor, for example an electric motor, can be provided in the handpiece part for driving of the treatment tool.

The supply media may be air, in particular compressed air or cooling air and/or a cooling medium, for example in the form of water or a spray, and/or current and/or light.

The coupling element, which may be arranged on the supply hose, can in particular be fixedly connected to the supply hose, so that no separation is provided between the supply hose and the corresponding coupling element for the everyday medical handling. The corresponding coupling element can thus be provided so to speak "inseparably" on the supply hose.

By "axial" or "axial direction" there is indicated that direction which, with coupled connection between the handpiece part and the supply hose, extends in the region of the coupling centrally in the direction of the main axis of the (non-bent) supply hose or of the part of the handpiece part adjacent to the coupling.

The guide element may be, for example, a guide pin, in particular a guide pin which is arranged axially centrally on the coupling element concerned. The guide element may have a main extension in axial direction.

For the rotational movement in accordance with the invention for achieving the predetermined coupling position there is provided in particular a guided, for example guided by the guide element, rotational movement. With "coupling position" there is thereby designated a relative position of the two coupling elements in which a transmission of current, or if applicable the further supply media, is possible between the two coupling elements. In that the two coupling elements can in general be rotated relative to one another before achievement of the coupling position the handling of the coupling is facilitated. Through such a rotation an attainment of the coupling position is possible without visual monitoring of the rotation process being necessary by the operating person, that is for example a dentist, carrying it out. Thus it is in particular not required upon insertion of the guide element into the insertion opening that the two coupling elements must be brought, with reference to the axial direction, to a certain rotational position relative to one another. They can thus be inserted into one another oriented, seen radially, arbitrarily. The insertion movement must thus, in particular in its end phase, be monitored only in one degree of freedom, to be more precise in axial direction; in contrast, in accordance with the state of the art, monitoring in two degrees of freedom, namely axial and radial, is required. In the case of the advantageous development in which, with inserted guide element, the two coupling elements are arrested in axial direction, there is provided a particularly simple handling in the manual production of the coupling connection.

The axis of rotation can in particular be oriented in axial direction. The direction of the axis of rotation may thereby be identical with the axial direction. Furthermore, the axis of rotation may run within the two coupling elements, for example centrally.

Further advantageously in this case, a pushing element is mounted movably and in sprung manner on the first coupling element and there is formed on the second coupling element a recess into which the pushing element can engage in sprung manner, whereby with inserted guide element the pushing element engages into the recess only in the predetermined coupling position of the two coupling elements relative to one another. Through this an operating person can be provided in a simple manner with an easily ascertainable, haptic indication as soon as the coupling position is attained.

The pushing element is advantageously movable parallel to the axis of rotation and mounted in the first coupling element. This makes possible a particularly space-saving configuration.

Advantageously there is arranged in or on the pushing element an electrical contact for the current supply of the handpiece part. Thereby the electrical contact can advantageously be constituted in the form of a jack, for example a slotted jack or a jack to jack adapter. Further, there is advantageously arranged on or in the pushing element a transmission device for the identification of the handpiece part. Here there may be involved for example at least one electrical contact.

By means of the above-mentioned pushing element, mounted in sprung manner, there is thus made possible a particularly comfortable handling of the coupling in accordance with the invention. It would be also conceivable in an alternative variant, however, that the pushing element is not mounted in sprung manner, but constituted in the form of a fixed projection instead. In this case the two coupling elements are first partly brought together axially and in this arrangement rotated with respect to one another for so long until the intended coupling position is attained. At this time, the coupling elements are then pushed together fully and therewith the connection made between the two elements. The handling is still improved in comparison with solutions from the state of the art with which the two coupling elements must be joined together from the beginning in the correct rotational disposition.

Advantageously there is arranged on that coupling element which is arranged on the supply hose a light source, for example in form of a high-pressure lamp or an LED.

Advantageously there is provided a latching device which, with inserted guide element, connects the two coupling elements with one another in a latched manner. It can thus be provided that the latch serves for axial arresting with inserted guide element. The latching device may include a latching ring or a groove and one or several latching sleeves or balls, whereby the latching ring or the groove is arranged on one of the two coupling elements and the latching sleeve(s) or ball(s) on the other coupling element. With such a latching device it can be achieved that the two coupling elements are, with inserted guide element, arrested in axial direction, but can however be generally rotated relative to one another, and this around an axis of rotation oriented in axial direction.

Advantageously there is arranged in the coupling at least one additional line for a supply medium for the handpiece part, for example a line for compressed air or a cooling medium. Thereby, advantageously, a non-return valve is arranged in this line.

In accordance with a further aspect of the invention there is provided a dental device which includes a handpiece part and a supply hose as well as a coupling in accordance with the present invention, in which the coupling element which can be arranged on the supply hose is connectable directly with the supply hose and/or the coupling element which can be arranged on the handpiece part is directly connectable for example by means of a screw connection with the handpiece part.

Advantageously the handpiece part includes in this case a drive motor, for example in form of an electric motor.

BRIEF DESCRIPTION OF THE DRAWINGS

The invention will be described below in more detail with reference to an embodiment and with reference to the drawings. There is shown:

FIG. 1 a perspective view of an embodiment of a first and second coupling element in accordance with the invention, FIG. 2 a further perspective view of the second coupling element, FIG. 3 a further perspective view the first coupling element, FIG. 4 a longitudinal sectional illustration of two coupling elements in the coupled condition, FIG. 5 a cross-sectional illustration of a first coupling element, FIG. 6 a horizontal section through two coupling elements, FIG. 7 a detail of the illustration of FIG. 6, FIG. 8 a vertical section through a first coupling element, FIG. 9 a detail of the illustration of FIG. 8, FIG. 9a the more detailed configuration of a single contact, FIG. 10 a cross-section through two coupling elements and adjacent parts of a handpiece part and a supply hose, FIG. 11 a partially transparent, perspective view of a first coupling element, FIG. 12 a perspective view of a handpiece part with a second coupling element, FIG. 13 a perspective view of a first coupling element connected with a supply hose, FIG. 14 a partially transparent, perspective view of a handpiece part and a second coupling element, and FIG. 15 a perspective view of a first coupling element and the adjacent part of a supply hose.

DETAILED DESCRIPTION

Figure 4:
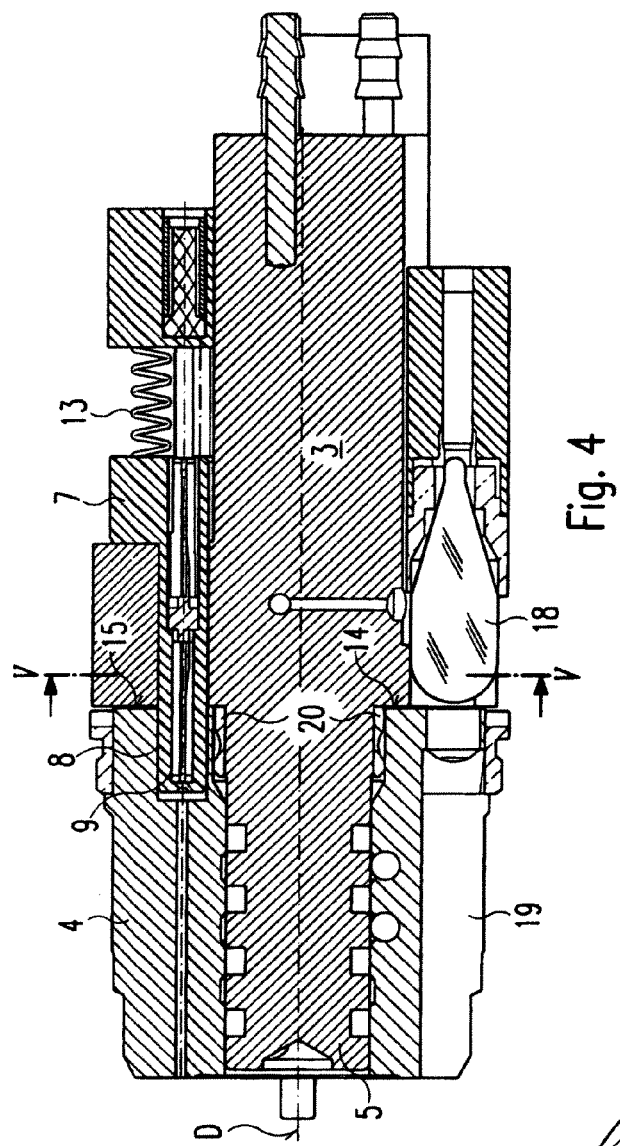

The illustration of FIG. 1 shows a perspective view of an embodiment of a coupling in accordance with the invention. The coupling serves for the production of a releasable connection between a medical, in particular dental, handpiece part and a supply hose, as well as for the transmission of current and if applicable further supply media from the supply hose to the handpiece part.

The coupling includes a first coupling element 3 and a second coupling element 4. In the illustrated embodiment the first coupling element 3 can be arranged on a supply hose and the second coupling element 4 on a handpiece part.

A further illustration of the second coupling element 4 is shown from another perspective in FIG. 2. A further illustration of the first coupling element 3 is shown from another perspective in FIG. 3.

The two coupling elements 3, 4 have each a substantially cylindrical form. As main axes of the coupling elements 3, 4 there will be designated in the following the main axes of the corresponding cylinders. The first coupling element 3 has a front side 14. The second coupling element 4 has a front side 15. The front sides 14, 15 are formed substantially planar and stand each normal to the respective main axis.

On the first coupling element 3 there is arranged a guide element 5 in form of a guide pin. The guide element 5 is elongate and projects, with reference to the front side 14 of the first coupling element 3, centrally in the direction of the main axis.

In the second coupling element 4 on the front side 15 there is formed an insertion opening 6 which is formed substantially congruently to the guide element 3, such that the guide element 5 can be inserted or plugged in lengthwise into the insertion opening 6.

The guide element 5 can be inserted into the insertion opening 6 so far until the front side 14 of the first coupling element 3 areally contacts the front side 15 of the second coupling element. In FIG. 4 the condition is represented, in longitudinal section, in which the guide element 5 is completely inserted into the insertion opening 6 and the two front sides 14, 15 are in contact. One recognizes that with inserted guide element 5 the two main axes of the coupling elements 3, 4 coincide.

Figure 12:
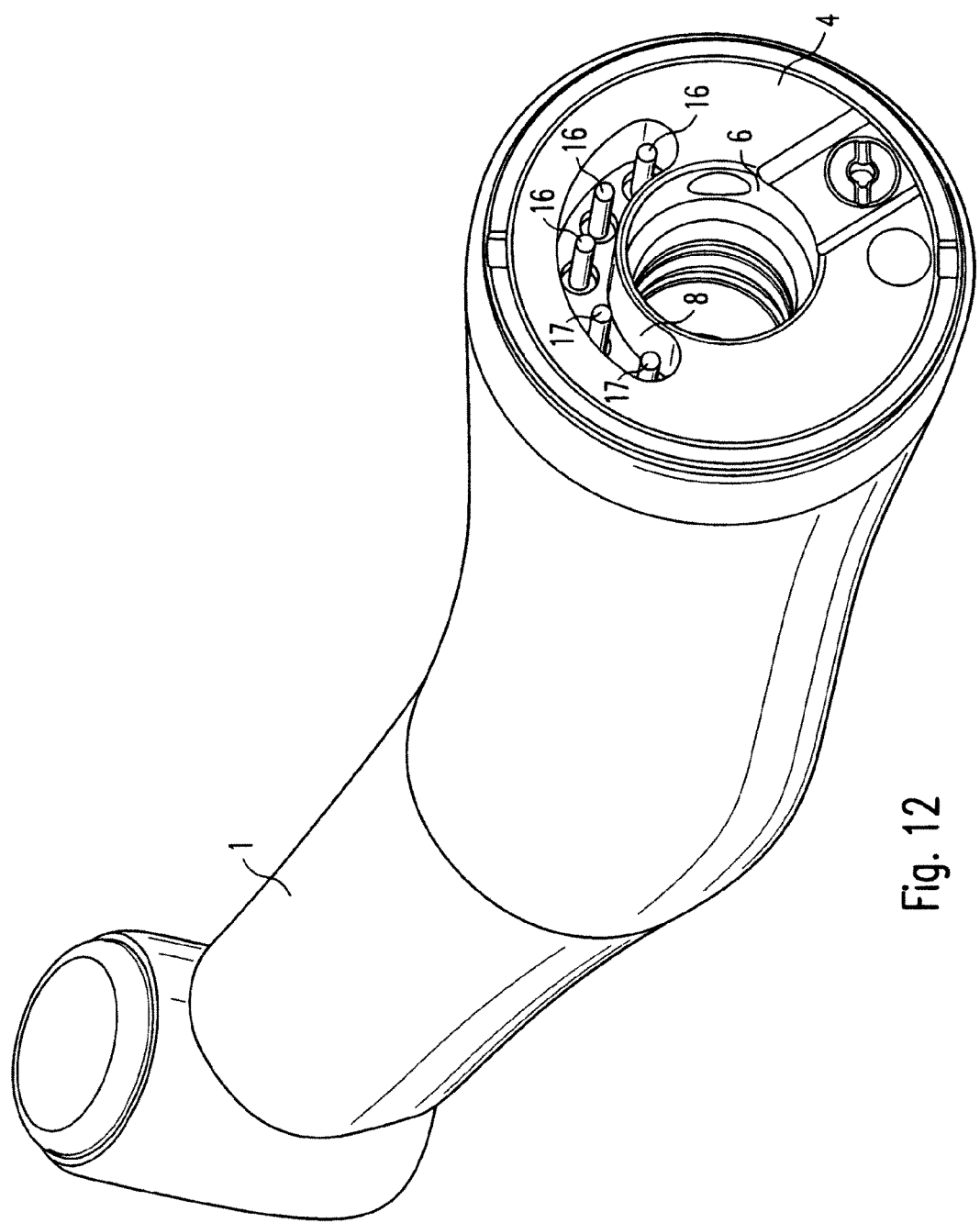
Figure 15:
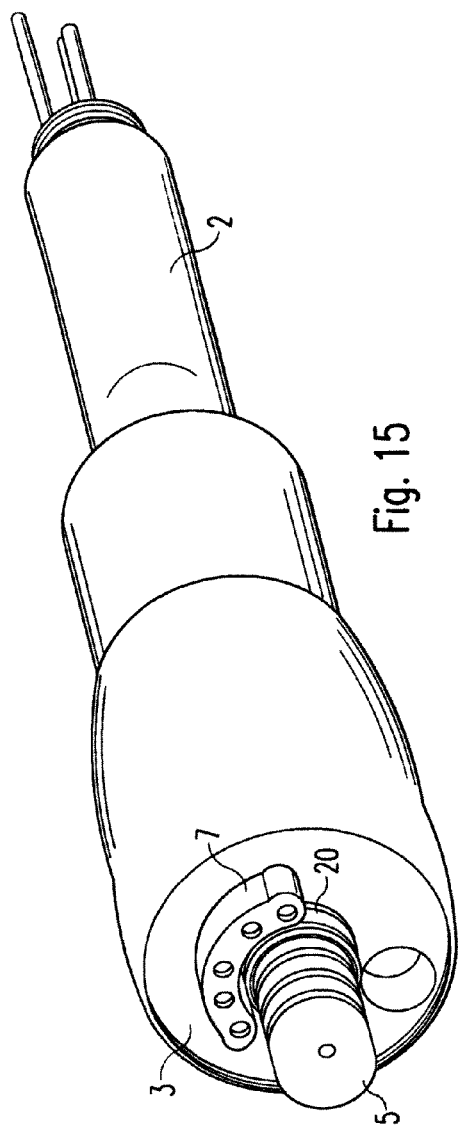

FIG. 15 shows the first coupling element 3 connected with a supply hose 2. In this connection the supply hose 2 extends (in non-bent condition) in the direction of the main axis of the first coupling element 3. FIG. 12 shows the second coupling element 4 connected with a handpiece part 1. The section of the handpiece part 1 adjacent to the second coupling element 4 thereby extends in the direction of the main axis of the second coupling element 4.

Figure 10:
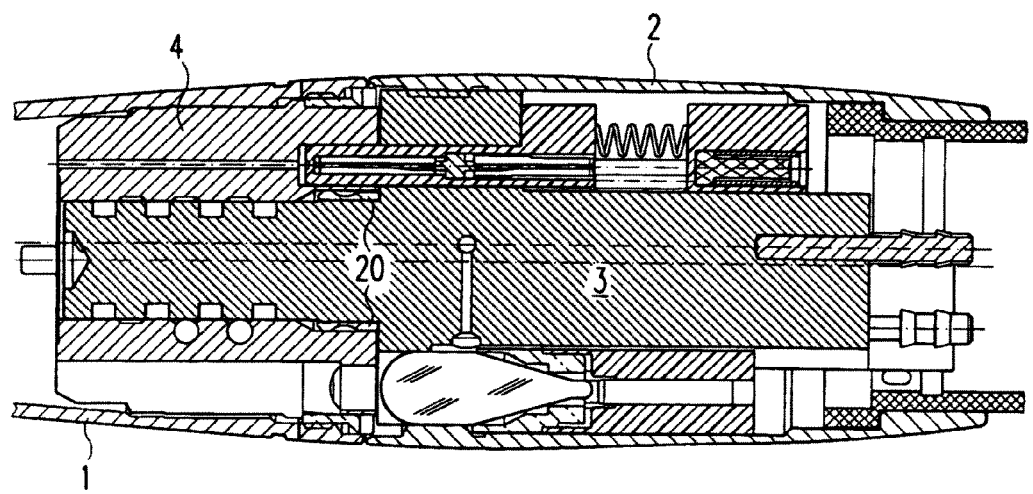

FIG. 10 represents a longitudinal section, in which the two coupling elements 3, 4 can be recognized in the condition in which they are connected to the supply hose 2 or the handpiece 1. In accordance with the embodiment the first coupling element 3 is fixedly connected—that is, so to speak "inseparably"—with the supply hose 2.

By "axially" there is designated the direction (or opposite direction which is determined by the two main axes of the coupling elements 3, 4 when the guide element 5 is inserted into the insertion opening 6.

Figure 13:
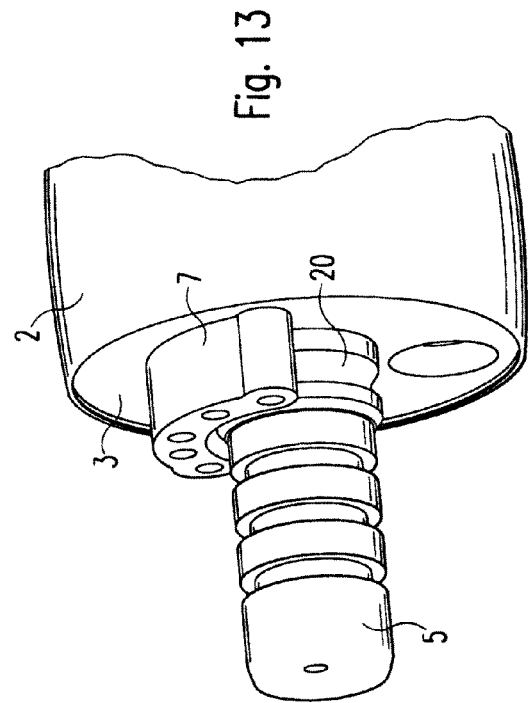

In accordance with a particularly preferred embodiment, with inserted guide element 5, the two coupling elements 3, 4 are arrested in axial direction. For this there serves a latching device 10 recognizable in FIG. 6. The latching device 10 has on the side of one of the two coupling elements, here on the side of the first coupling element 3, a latching ring 20 with a circumferential groove, closed in the circumferential direction, and has on the side of the other coupling element, here the second coupling element 4, at least one latching sleeve 21 which is mounted in sprung manner and can engage into the groove of the latching ring 20 in sprung manner. The latching ring 20 can be recognized inter alia in FIGS. 13 and 15. One recognizes the latching sleeves 21 for example in FIG. 6 and in FIG. 7 which represents an enlarged detail of FIG. 6. In the perspective views of FIGS. 1 and 2 the latching sleeve 21 is shown in removed condition, that is, separately.

The latching ring 20 and the latching sleeves 21 are so configured that upon insertion of the guide element 5 into the insertion opening 6 it is ascertainable, that is haptically perceptible, when the latching sleeve 21 engages into the latching ring 20, more precisely into the circumferential groove of the latching ring 20. Through this the handling of the coupling is further facilitated. As an alternative to the illustrated solution the latching could be effected also by means of a circumferential groove and one or a plurality of balls.

In the embodiment, the latching device 10 is formed or arranged such that the arresting in axial direction is effected shortly before the two front sides 14, 15 come into contact. This can be seen from the illustrations of FIGS. 4 and 6, for example. Through this in general upon insertion of the guide element 5 into the insertion opening 6 in the final phase of the movement there is supported a relative orientation of the two coupling elements 3, 4.

Through the configuration of the latching device 10 in form of the latching ring 20 with the circumferential groove and the latching sleeve 21, there is possible in general a relative rotation of the two coupling elements 3, 4 around an axis of rotation D in guided manner, wherein the axis of rotation D extends axially longitudinally of the main axes of the two coupling elements 3, 4. The axis of rotation D is designated in FIG. 4. However the mentioned rotation is not possible without restriction, but is merely possible to a restricted degree. This will be further considered below.

Figure 8:
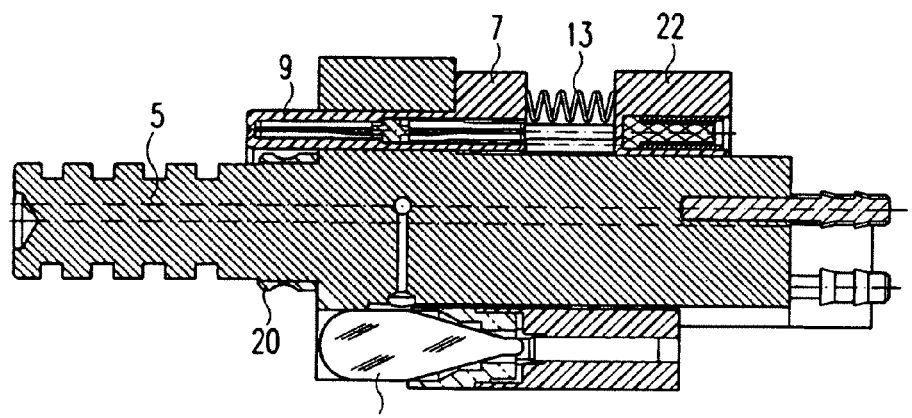
Figure 9:
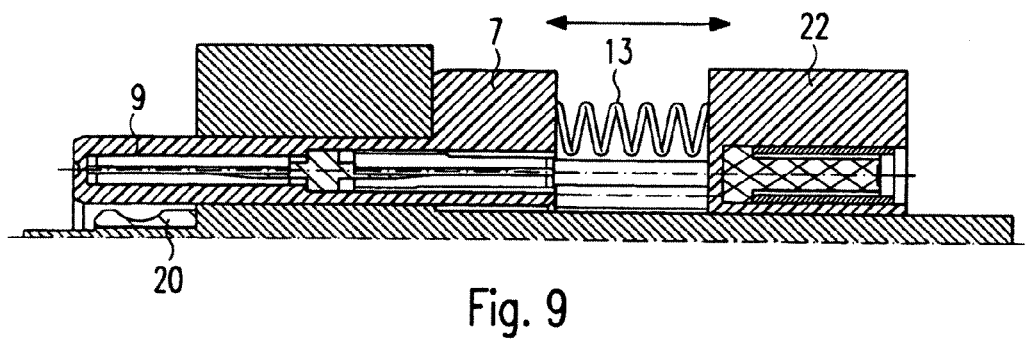

On the first coupling element 3 there is arranged a pushing element 7, for example of plastic, which is mounted movably and in sprung manner. In the embodiment, a spring 13 is provided for this, as can be recognized in the illustration of FIG. 4 for example. Further, the spring 13 can be recognized in FIG. 8, and in FIG. 9, which shows a detail of the illustration of the FIG. 8. (In the illustrations of FIGS. 1 and 3 this spring 13 is not illustrated.)

Due to the effect of the spring 13 the pushing element 7 projects axially beyond the front side 14 of the first coupling element 14 insofar as no external force acts on the pushing element 7. The pushing element 7 is mounted so movably on the first coupling element 3 that it can be moved parallel to the main axis of the first coupling element 3, this movement being effected, however, outside the main axis, that is not centrally with reference to the first coupling element 3. The pushing movement is indicated by a double arrow in FIG. 9.

The pushing element 7 is so mounted in sprung manner on the first coupling element 3 that it can be pushed manually so far against the force of the spring 13 until it no longer projects beyond the front side 14 of the first coupling element 3.

On the second coupling element 4 there is formed a recess 8, the shape of which is formed essentially congruently to that section of the pushing element 7, which—in the condition without action of external force—projects beyond the front side 14. The pushing element 7 can engage into the recess 8 in sprung manner, in particular with inserted guide pin 5 or in the condition in which the coupling elements are axially arrested. In the illustration of the FIG. 4 the condition is shown in which the pushing element 7 stands in engagement with the recess 8.

Since the form of the recess 8 is matched with the pushing element 7, there is an exact mutual rotational position of the two coupling elements 3, 4 in which the pushing element 7 engages into the recess 8 due to the action of the spring 13. This position is described as coupling position. Alternatively, however, also two or more recesses can be provided into which the pushing element 7 can engage. In this event two or more coupling positions are correspondingly possible.

If the two coupling elements 3, 4 are so inserted into one another—that is the guide element 5 inserted into the insertion opening 6—that the pushing element 7 and the recess 8 do not align, then after production of the axial arresting a relative rotation of the two coupling elements 3, 4 can be carried out. This rotation is, however, possible only up to the mentioned rotational position, which corresponds to the coupling position, because in this position the pushing element 7 engages into the recess 8 due to the force of the spring 13.

If the two coupling elements 3, 4 are so inserted into one another—that is, the guide element 5 inserted into the insertion opening 6—that the pushing element 7 and the recess 8 do not align, before attainment of the axial arresting the pushing element 7 is pushed back against the force of the spring 13 by the front side 15 of the second coupling element 4, and this so far until the pushing element 7 no longer projects beyond the front side 14 of the first coupling element 3. After attainment of the axial arresting a relative rotation of the two coupling elements 3, 4 can then be carried out until that rotational position is attained which corresponds to the coupling position. In this position the pushing element 7 snaps into the recess 8.

For the production of the connection, that is for the positioning of the two coupling elements 3, 4 in the coupling position, it is therefore merely necessary to insert the guide element 5 into the insertion opening 6 as far as axial arresting and then—so far as the two coupling elements 3, 4 in this condition are not yet in that relative rotational position which corresponds to the coupling position—carrying out a relative rotation of the two coupling elements 3, 4 with respect to one another, until the pushing element 7 engages into the recess 8.

This engagement can, as mentioned already, be so that configured it can be felt by an operating person. In addition, it also can be configured to be audible, for example in form of a clicking. Visual monitoring of the production of the coupling connection is therefore practically not necessary for the operating person. Merely in the initial phase of the insertion of the guide element 5 into the insertion opening 6 might a visual contact be helpful. For the following rotation which generally takes place no visual contact is now needed. After successful production of the coupling position it is indicated to the operating person haptically and acoustically that the connection is produced as desired. In comparison with conventional couplings, the operation of a coupling in accordance with the invention is thus possible considerably more simply and also more rapidly.

An alternative variant in accordance with the invention could also be formed in that the pushing element is not mounted in sprung manner but instead is constituted in form of a fixed projection. In this case the two coupling elements 3, 4 would be—so far as they are not yet in the relative rotational position which corresponds to the coupling position —initially be merely partly brought together axially and in this arrangement rotated with respect to one another for so long until the intended coupling position is attained. Only at this time are the coupling elements 3, 4 then pushed together completely and with that the connection made between the two elements.

Further, the arrangement of the pushing element could of course also be effected on the coupling element on the instrument side, whereby the coupling part on the tube side must then be correspondingly modified.

Figure 9A:
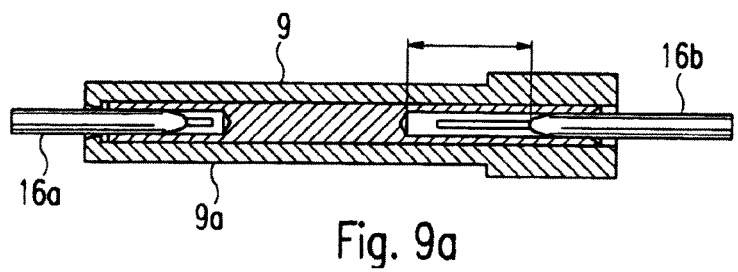

In the embodiment, electrical contacts 9 for the current supply of the handpiece part 1 are arranged in the pushing element 7. The electrical contacts 9 are constituted in the form of jacks, more precisely as jack to jack adapters 9a. For engagement in the jack to jack adapters 9a contact pins 16a are provided on the side of the second contact element 4, which for example are illustrated in FIG. 12. These contact pins are not indicated in the illustration of FIG. 4 for reasons of clarity. Corresponding contact pins or studs 16b are provided also on the first coupling element 3, as the illustration of a single contact 9 in FIG. 9a shows. The arrow illustrated in FIG. 9a represents the displacement path of the corresponding contact pin. On the other side of the spring, which is connected at its one end with the contact pins 16b, there is arranged on the first coupling element 3 a corresponding plug receiver 22.

In that the coupling position is provided in an unambiguous rotational position, the electrical contacting can be particularly reliably configured. Damage to the contacts can be excluded to the greatest extent. The configuration in the form of the contact pin 16a and 16b on the one hand and electrical contacts 9 in the form of jack to jack adapters on the other hand makes this possible particularly favorably.

As can be understood from FIG. 12, in the embodiment there are provided three electrical contact pins 16a, for the current supply of an electric motor which is arranged in the handpiece part 1 or is connected to the handpiece part. This is preferably a so-called collectorless motor, wherein via the contacts 9 formed through this the stator windings of the motor are provided with voltage. If, in contrast, a collector motor were used, a current supply via merely two contacts would be sufficient.

Alongside this, two further contact pins or contacts are provided, which represent a transmission device for the identification of the handpiece part 1. For this purpose there may be provided for example in the handpiece part 1 an electrical resistor element, which on both sides is connected in each case with one of contact pins of the transmission device 17, so that with the aid of a corresponding current flow a resistance can be detected which makes the handpiece part 1 identifiable. In this way a coupling in accordance with the invention is suitable in general for handpiece parts of different kinds.

With the aid of the contacts formed by a jack to jack adapter and two contact pins a particularly good and reliable current supply or general electrical contacting is ensured. As an alternative to this, the electrical contacts could, however, also be configured in the form of blunt contacts and spring-mounted pins.

As illustrated for example in FIG. 4, there is further arranged on the first coupling element 3 a light source in form of a high-pressure lamp 18. On the side of the second coupling element 4 there is provided—in the coupling position, lying opposite—a corresponding light guide 19 with the aid of which the light is guided to the head of the handpiece part 1. This can be seen best from FIG. 14.

Figure 6:
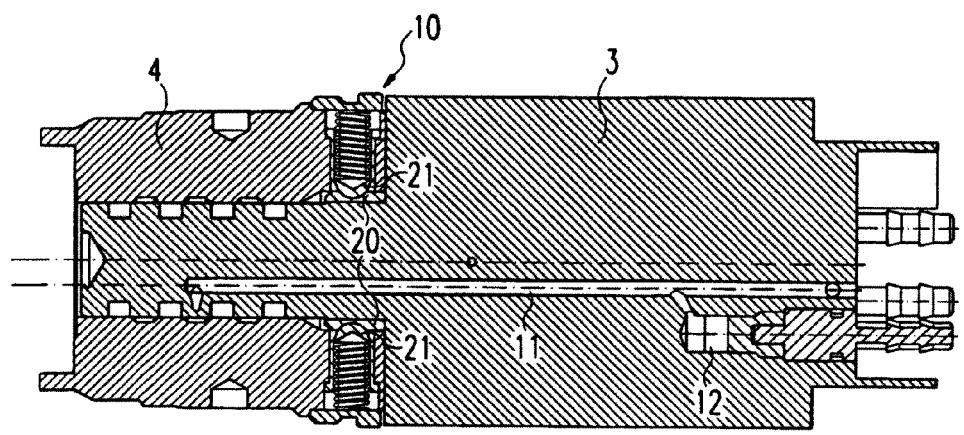
Figure 7:
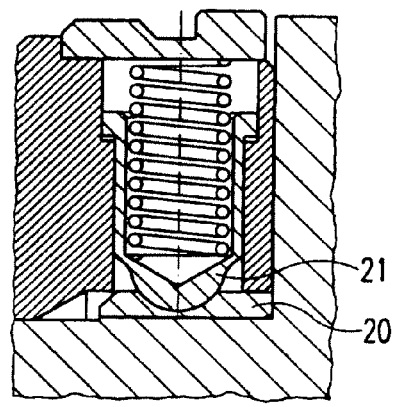

Further, in the embodiment there is provided a line 11 for a cooling medium for example in form of a spray or cooling air. In the illustration of FIG. 6 one recognizes the section of this line 11 on the side of the first coupling element 3. The corresponding connection to the section of the line 11 in the second coupling element 4 is effected in per se known manner via a ring groove connection. Such a connection is known as such from the state of the art, for example from the German laid open document DE 32 15 207 A1. In the illustration of FIG. 14 one recognizes the further course of the line 11 in the handpiece part 1. As can be recognized from FIG. 6, a non-return valve 12 is provided in the line 11. Several lines can in general be provided. Thus, for example, a line for a spray and a further line for cooling air can be provided. Also the return of the cooling air from the handpiece back to the supply unit situated at the other end of the line would be possible with the aid of a further line.

Figure 11:
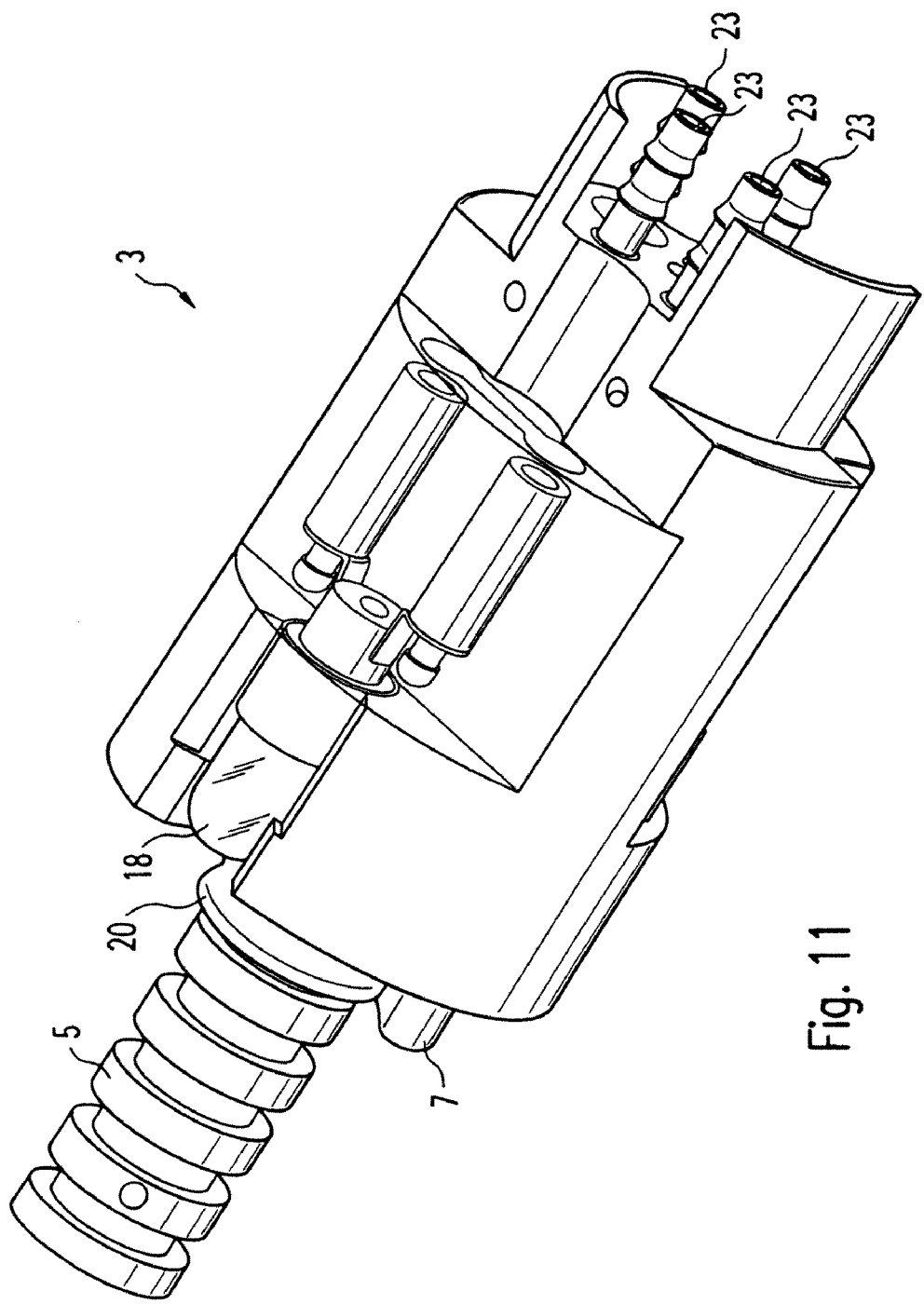

In FIG. 11 one recognizes arranged on the first coupling element 3 steel nipples 23 for connection with hoses (not shown) which serve for the passing on of corresponding media in the supply hose.

In the embodiment it is thus provided that the coupling serves for the connection on the one hand of a handpiece part, which is connected with an electric motor or which contains an electric motor, and a supply hose on the other hand, wherein in the coupling position the following supply media can be transmitted: current for the motor, current or electrical signals for the recognition or identification of the handpiece, spray, cooling air, return cooling air and light.

Figure 5:
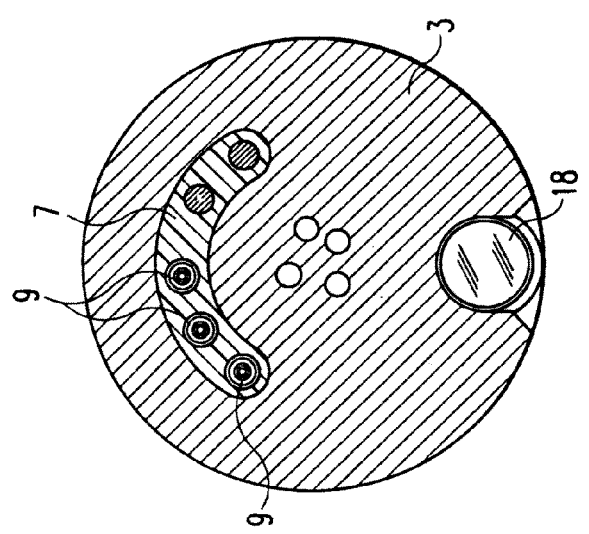

In FIG. 5 there is shown the section V-V in accordance with FIG. 4. Among other things one recognizes the high-pressure lamp 18 and the electrical contacts 9 for the current supply of the handpiece part 1. The high-pressure lamp 18 is also shown in perspective in the illustration of FIG. 11, wherein as an alternative light source an LED could also be used.

LIST OF REFERENCE SIGNS 1 handpiece part
2 supply hose
3 first coupling element
4 second coupling element
5 guide element
6 insertion opening 7 pushing element
8 recess
9 electrical contact
9a jack to jack adapter
10 latching device
11 line for a cooling medium
12 non-return valve
13 spring
14 front side of the first coupling element
15 front side of the second coupling element
16a instrument-side contact pin for the current supply of the handpiece part
16b hose-side contact pin for the current supply of the handpiece part
17 contact pin for handpiece identification
18 high-pressure lamp
19 light guide
20 latching ring
21 latching sleeves
D axis of rotation

The invention claimed is:

1. A coupling assembly for connecting a dental handpiece having an electric motor therein to a supply hose for providing electrical power to the handpiece, comprising:
   a first coupling member having an insertion opening;
   a second coupling member having a guide element wherein the guide element is configured to be received within the insertion opening;
   a pushing element formed on the first coupling member and having a first electrical contact, the pushing element being connected to the guide element and movably mounted on the second coupling member for axial movement along the second coupling member between an extended position in which the guide element constitutes a leading edge of the second coupling member, and a retracted position;
   a resilient biasing member on the second coupling member acting on the pushing member to bias the guide element to its extended position;
   a recess sized and configured to receive the pushing element, wherein the recess is formed on the second coupling member and includes a second electrical contact, wherein the pushing element and the recess are configured and sized relative to each other to bring the first and second electrical contacts into register when the pushing element is inserted into the recess, and wherein the guide element is received in the insertion opening to bring the first and second electrical contacts into engagement when the first and second coupling members are coupled together with the insertion opening and the guide element coupling members being rotated to a predetermined rotational orientation such that the pushing element is inserted into the recess and the guide member is at a predetermined axial depth in the insertion opening; and
   a latching mechanism for detachably securing the first and second coupling members together against axial forces tending to separate them when the coupling members are brought into engagement, with the guide element received in the insertion opening.

2. The coupling assembly of claim 1, wherein the guide element and the insertion opening prevent further axial movement the coupling members when the guide element is received in the insertion opening.

3. The coupling assembly of claim 1, wherein one of said first and second electrical contacts comprises a contact pin and the other electrical contact comprises a corresponding plug for receiving the contact pin in electrical engagement when the guide element is received in the insertion opening at the predetermined axial depth.

4. The coupling assembly of claim 3, wherein the contact pin is spring loaded and the plug is a blunt contact for electrically coupling with the contact pin when the coupling members are engaged at the predetermined axial depth and the predetermined rotational orientation.

5. The coupling assembly of claim 1, wherein the first coupling member is connected to the supply line and the second coupling member is connected to the handpiece.

6. The coupling assembly of claim 1, wherein the first coupling member is connected to the handpiece and the second coupling member is connected to the supply hose.

7. The coupling assembly of claim 1, wherein one of said first and second coupling members further comprises a light source.

8. The coupling assembly of claim 7, wherein the other of said coupling members comprises a light guide for receiving light from the light source and directing the light to a head of the handpiece.

9. The coupling assembly of claim 1 wherein the latching mechanism comprises a latching sleeve movably mounted on one of said coupling members and a latching ring with a circumferential groove on the other of said coupling members, with the latching sleeve being biased to a position in which the latching sleeve will engage the circumferential groove to hold the coupling members in engagement upon being moved into engagement.

10. The coupling assembly of claim 9, wherein the latching sleeve houses a spring for biasing the latching sleeve to a latching ring engagement position.

11. The coupling assembly of claim 1, further comprising a fluid supply line for supplying a fluid medium to the handpiece from the supply line when the guide element is received in the insertion opening at the predetermined axial depth.

12. The coupling assembly of claim 11, further comprising a seal at engaging faces of the coupling members to define a sealed flow path for the fluid as it flows between the first and second coupling members.

13. The coupling assembly of claim 1, wherein the first and second coupling members are free to rotate relative to each other until the pushing element engages the recess.

14. The coupling assembly of claim 1, wherein the pushing element and resilient biasing element provide a non-visual indication to an operator when the first and second coupling members are coupled and rotated into the predetermined rotational orientation and the guide element is at a predetermined axial depth.

15. The coupling assembly of claim 14, wherein the non-visual indication is a tactile indicator.

16. The coupling assembly of claim 14, wherein the non-visual indication is an audible indicator.

17. The coupling assembly of claim 1, wherein at least one of the electrical contacts is configured as a transmission device for indicating the identity of the handpiece when the first and second coupling members are brought into engagement.

18. The coupling assembly of claim 17, wherein the transmission device comprises:
   an electrical resistor element having a predetermined electrical resistance corresponding to a predetermined model of handpiece;
   a current flow through the resistor element; and
   means for measuring the resistance of the current flow for determining the identity of the handpiece.

* * * * *